United States Patent [19]

Reutelingsperger et al.

[11] Patent Number: 5,258,497
[45] Date of Patent: Nov. 2, 1993

[54] PROCESS FOR PURIFYING ANNEXINES

[75] Inventors: Christiaan Reutelingsperger, Maastricht, Netherlands; Gerhard Bodo, Wien, Austria

[73] Assignee: Boehringer Ingelheim International GmbH, Fed. Rep. of Germany

[21] Appl. No.: 552,172

[22] Filed: Jul. 13, 1990

[30] Foreign Application Priority Data

Jul. 15, 1989 [DE] Fed. Rep. of Germany ....... 3923501

[51] Int. Cl.[5] .................. C07K 3/02; C07K 15/06; C07K 15/16
[52] U.S. Cl. .................. 530/350; 530/359; 530/415; 530/423; 530/425
[58] Field of Search ............ 530/350, 412, 418, 419, 530/420, 415, 422, 359, 423, 425

[56] References Cited

U.S. PATENT DOCUMENTS

| | | | |
|---|---|---|---|
| 4,507,229 | 3/1985 | Bohn et al. | 260/112 B |
| 4,683,294 | 7/1987 | Van Wijnendaele et al. | 530/371 |
| 4,736,018 | 4/1988 | Reutelingsperger | 514/2 |
| 4,937,324 | 6/1990 | Fujikawa | 530/851 |

OTHER PUBLICATIONS

DiRosa et al., *Prostaglandins* 28:441-442 (1984).
Geisow et al. *Biochem. Soc. Transactions* 15:800-802 (1987).
Hirata et al. *Biol. Chem.* 256:7730-7733 (1981).
Kaetzel et al. *The Journal of Biological Chemistry* 264:14463-14470 (Aug. 25, 1989).
Maki et al., *Eur. J. Obstet. Gyn. Reprd. Biol.* 17:149-154 (1984).
Maurer-Fogy et al., *Eur. J. Biochem.* 174:585-592 (1988).
Miller-Anderson et al. *Thromb. Res.* 5:439-452 (1974).
Reutelingsperger et al. *Eur. J. Biochem.* 173:171-178 (1988).
Schapira et al. *Biochemistry* 20:2738-2743 (1981).
Shitara et al. *Blood and Vessel* 14:498-500 (1983), and an unverified English translation thereof.
Tait et al. *Biochem.* 27:6268-6276 (1988).
Geisow et al., *The EMBO Journal* 3(12):2969-2974 (1984).

*Primary Examiner*—Jeffrey E. Russel
*Attorney, Agent, or Firm*—Sterne, Kessler, Goldstein & Fox

[57] ABSTRACT

The present invention relates to processes for purifying annexines. The overall process includes the steps of preparing a homogenized cell preparation and adjusting the pH to about 8.0 to 10.0, adding at least one bivalent cation, adding a phospholipid, washing the insoluble cell residue to remove the soluble constituents, and extracting the annexines from the cell residue with a chelating agent. This process initially promotes the adsorption of the annexines onto the insoluble cell residue or membrane of the host organism. The adsorption step makes it possible to eliminate unwanted soluble matter from the homogenized material by simple washing. Desorption is accomplished by using a chelating agent.

20 Claims, 2 Drawing Sheets

PROCESS FOR PURIFYING ANNEXINES

FIELD OF THE INVENTION

The present invention is in the field of medicinal chemistry. In particular, the present invention relates to improved processes for the purification of annexines as well as the substantially pure annexines obtained thereby.

BACKGROUND OF THE INVENTION

In the majority of mammals there are proteins which have anti-coagulant properties. These proteins can be divided, as follows, into three groups based on their different mechanisms of activity:

1. Proteins which form a complex with the coagulating factor and thereby render the coagulating factor ineffective. These include the following proteins:
   a) Anti-thrombin-III (*Thromb. Res.* 5:439–452 (1974))
   b) α-Protease Inhibitor (*Ann. Rev. Biochem.* 52: 655–709 (1983))
   c) α2-Macroglobulin (*Ann. Rev. Biochem.* 52:655–709 (1983))
   d) C1-Inhibitor (*Biochemistry* 20:2738–2743 (1981))
   e) Protease Nexin (*J. Biol. Chem.* 258:10439–10444 (1983)).
2. Proteins which proteolytically cut up a coagulation factor and thereby inactivate the coagulation factor. The only protein of this kind which has hitherto been described is protein C (*J. Biol. Chem.* 251:355–363 (1976)).
3. proteins which screen off and/or hydrolyse the negatively charged phospholipids, so that the phospholipid-dependent reactions of the coagulation mechanism are inhibited. Hitherto, only phospholipases isolated from various types of snake venom have been described (*Eur. J. Biochem.* 112:25–32 (1980)).

The coagulation system, which proceeds step by step, has been intensively investigated in recent years. It is understood to be a self-intensifying multi-step system of various interconnected proteolytic reactions in which one enzyme converts a zymogen into the active form (cf. Jackson C. M., Nemerson Y., *Ann. Rev. Biochem.* 49:765–811 (1980)). The speed of this reaction is critically increased by the presence of phospholipids and other co-factors such as factor Va and factor VIIIa. In vivo, the pro-coagulation reactions are regulated by various inhibiting mechanisms which prevent an explosively thrombotic trauma after slight activation of the coagulation cascade.

The anti-coagulation mechanism can be sub-divided as follows (Rosenberg, R. D., Rosenberg, J. S., *J. Clin. Invest.* 74:1–6 (1984)):

1. The serine protease factor Xa and thrombin are inactivated as a result of binding to anti-thrombin III or to the anti-thrombin/heparin complex. Both the prothrombin activation and also the formation of fibrin can be inhibited in this way. In addition to anti-thrombin III, there are various other plasma-protease inhibitors such as, for example, α2 macroglobulin and anti-trypsin, the effect of which is dependent on time.
2. The discovering of protein C resulted in the discovery of another anti-coagulation mechanism. Once protein C has been activated, it acts as an anti-coagulant by selective proteolysis of the protein co-factors factor Va and VIIIa, by means of which prothrombinase and the enzyme which reacts with factor X are inactivated.
3. Plasmin cleaves monomeric fibrin 1, a product of the action of thrombin on fibrinogen, thereby preventing the formation of an insoluble fibrin (Nosssel, H. L., *Nature* 291: 165–167 (1981)).

Of the native proteins involved in the coagulation process mentioned above, only anti-thrombin III is currently in clinical use. However, a serious disadvantage of the use of this protein is the increased tendency to bleeding.

All of the agents hitherto used as anti-coagulants, be they native or synthetic by nature, render the coagulation factors inactive in some way and thereby produce side effects which may have a disadvantageous effect on the coagulation process.

Surprisingly, in addition to these proteins, other native substances have been isolated which still show the desired anti-coagulant properties under particular conditions but do not increase the risk of bleeding. In the case of major bleeding, these proteins lose their anti-coagulant properties and consequently, in such cases, their use does not interfere with the coagulation processes necessary for survival. As they were first isolated from strongly vascularized tissue they are known as vascular anti-coagulating proteins, VAC.

The proteins isolated from strongly vascularized tissues such as umbilical cord vessels and placenta have molecular weights of about $70 \times 10^3$, about $60 \times 10^3$, about $34 \times 10^3$ and about $32 \times 10^3$, of which the substances with the molecular weights of 34 and $32 \times 10^3$ consist of a single polypeptide chain. The precise biochemical characterization of these proteins and the methods for isolating and purifying them can be found in EP-A-0 181 465, which is incorporated by reference herein in its entirety.

Proteins with a VAC activity are natural blood coagulation inhibitors which interfere with the blood coagulation cascade at two points. The first time, they inhibit the activation of factor X into Xa, catalyzed by factors IXa and VIIIa, and the second time they suppress the cleaving of prothrombin to form thrombin, which is mediated by factors Xa and Va. One fact common to both activation steps is that they require calcium ions and phospholipids. Obviously, VAC proteins are also able to interact with phospholipids and, as a result of this binding, block the activation steps of the coagulating factors.

It has been found in the meantime that there is a whole family of substances which, like VAC, bind to phospholipids in a calcium-dependent manner and interfere with processes dependent on phospholipid surfaces. This family, which is also known as the annexines, includes not only lipocortin I, calpactin I, protein II, lipocortin III, p67-calelectrin but also IBC, PAP, PAP I, PP4, endonexin II and lipocortin V.

The common structural features of the annexines probably form the basis for their similar Ca2+ and phospholipid binding properties. Although this general property is true of all annexines, there is a clear individuality with regard to their affinity for Ca2+ and the various types of phospholipid.

The physiological functions of the annexines are concerned with membrane-associated processes. The basic mechanism of the anti-coagulant effect of VAC has been recognized as the inhibition of the catalytic capacity of phospholipids by binding VAC to the surface thereof, thus preventing the formation of the coagulation-promoting complex on the surface.

Other annexines are also capable of inhibiting coagulation, but VAC appears to be the most effective inhibitor.

Binding studies have shown that VAC associates reversibly with pro-coagulatory phospholipids, in calcium dependent manner. Other bivalent cations selected from the series $Cd^{2+}$, $Zn^{2+}$, $Mn^{2+}$ and $Co^{2+}$ also have a positive effect on association, but not to the same extent as $Ca^{2+}$.

These properties make the proteins interesting and extremely valuable active substances from a pharmacological point of view. The genetic engineering method which made it possible to produce VAC proteins is described in EPA 293 567, the disclosure of which is fully incorporated by reference herein.

In the process disclosed in EPA 293 567, the frozen biomass was suspended in a suitable lysing buffer in order to isolate and purify the expressed proteins. The cells were then mechanically destroyed, for example, using a Manton-Gaulin press. After the addition of a precipitating agent for non-protein constituents such as polyethylenimine, the solid constituents were removed, for example, by centrifugation. After precipitation of the proteins, preferably by ammonium sulphate fractionation, dissolving the precipitate, removing the precipitating agent and clarifying the solution, the extract thus obtained was subjected to various chromatographic purification procedures. Instead of precipitation of proteins, the crude VAC extract can also be purified by chromatographic pre-purification provided that it can then be subjected to a later cleaning cycle. $SiO_2$ has proved suitable as the column material for the pre-purification, for example, but other materials with similar properties are also suitable. According to the invention, silica catalyst carrier grade 953 W made by Messrs Grace was used.

A chromatographic purification cycle suitable for purifying the proteins according to the invention consisted, for example, of a DEAE-Fast-Flow-Sepharose, a sephacryl S-200 high resolution and a Q-Sepharose-Fast-Flow-Chromatography. The purity of the proteins according to the invention obtained in this way was determined by SDS-PAGE, western blot, gel permeation HPLC, reverse HPLC and isoelectric focusing.

SUMMARY OF THE INVENTION

It is an object of the present invention to improve the process described in EPA 293 567 for isolating and purifying VAC proteins.

In particular, the invention relates to a process for purifying an annexine, comprising the steps of:
a) obtaining cells which express an annexine,
b) homogenizing said cells and adjusting the pH to about 8.0 to about 10.0,
c) adding at least one bivalent cation selected from the group $Ca^{2+}$, $Cd^{2+}$, $Zn^{2+}$, $Mn^{2+}$ and $Co^{2+}$,
d) adding a phospholipid,
e) washing the insoluble cell residue to remove the soluble constituents, and
f) extracting the annexine from the cell residue with a chelating agent.

In particular, the invention relates to a process for purifying a VAC, comprising the steps of:
a) obtaining cells which express a VAC,
b) inactivating and homogenizing said cells and adjusting the pH to about 9.0,
c) adding $Ca^{2+}$,
d) adding lecithin,
e) washing the insoluble cell residue to remove the soluble constituents, and
f) extracting the VAC from the cell residue with EDTA.

The invention also relates to the substantially pure annexines and VAC proteins obtained according to the processes of the invention.

DESCRIPTION OF THE PREFERRED EMBODIMENTS

Figure 1:
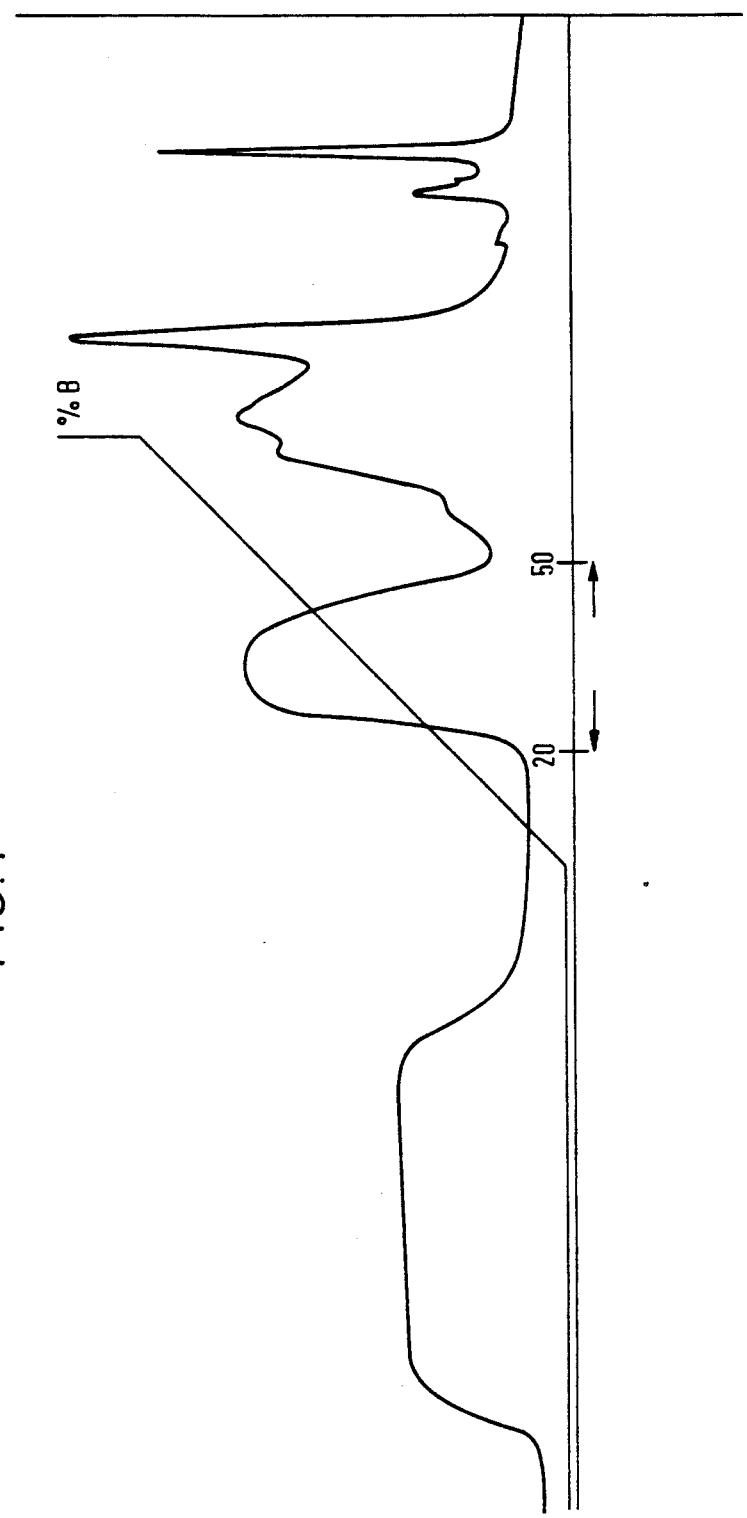
FIG. 1 depicts a chromatography elution profile on Phenyl-20 Sepharose Fast Flow (←→=VAC-Pool).

The lysing and extraction step according to EPA 293 567 gave a yield of about 50% of the material which required further purification. By improving this step according to the present invention, it is surprisingly possible to increase the yield after this step to more than 80%.

In one aspect, the present invention provides a process for purifying an annexine comprising the steps of:
a) adjusting the pH of the homogenized cellular material to about 8.0 to about 10.0;
b) adding at least one bivalent cation selected from the art. group consisting of $Ca^{2+}$, $Cd^{2+}$, $Zn^{2+}$, $Mn^{2+}$ and $Co^{2+}$;
c) adding a phospholipid;
d) washing the insoluble cell residue to remove soluble constituents; and
e) extracting the annexines from the cell residue using chelating agents.

The process according to the invention ensures that the annexines, e.g., VAC proteins, are adsorbed onto the insoluble cell residue or membrane of the host organism, which is preferably E. coli. This in situ adsorption step surprisingly makes it possible to eliminate unwanted soluble matter from the homogenized material by simply washing the insoluble cell residue. Desorption of the annexines, e.g. VAC proteins, bound to the solid "carrier" is accomplished using chelating agents which preferably comprise a buffer and EDTA.

Advantageously, a mixture of bivalent cations may be used, for example, $Ca^{2+}$ in conjunction with $Zn^{2+}$, the molar ratios of each cation being adjusted to maximize adsorption of the annexine, such as VAC, onto the insoluble cell residue.

Surprisingly, when the annexines which had been prepared by expression in E. coli were purified, the amount of E. coli protein (ECP) could be reduced significantly by the addition of a resin with ionizable groups, preferably strongly cationic groups such as BPA (Bioprocessing Aids, made by Tosohaas, Stuttgart, Germany). For example, BPA-100 (a crosslinked polymethylacrylate ester functionalized with cationic groups (tertiary amines)), BPA-2100 (a divinylbenzol-crosslinked polystyrene functionalized with strongly anionic groups (sulfonic acids)), preferably BPA 1000, was added to the crude extract obtained after EDTA extraction, and then stirred. The amount added may be 1 to 20% by volume, preferably, 5 to 10, more especially 10% by volume. The precipitate is removed by centrifugation. This is followed by protein precipitation and chromatographic procedures. By adding BPA, it was possible to lower the ECP content even at this stage to only 2% of the initial level. The VAC content, on the other hand, was reduced by only 6%.

A further improvement in yield was surprisingly achieved by deactivating the cells of the fermentation mixture before the breaking up of the cells. The deactivation agents used may include simple aromatic compounds such as benzene, toluene, phenyl, xylene or cresol. It is particularly advantageous to use m-cresol.

By including this preliminary deactivation step, in conjunction with the procedure described hereinbefore, it was possible to increase the extraction yield to more than 98%!

By the term "substantially pure" is intended annexines having substantially one major component as measured by SDS-PAGE, western blot, gel permeation HPLC, reverse HPLC or isoelectric focusing.

The adsorption/desorption step is followed by the purification steps described in EPA 293 567, which is fully incorporated by reference herein. The parameters required for this such as temperature, quantities, sequence of the individual steps, pH values, particular reagents, etc, are well known to those skilled in the art. The examples which follow may be, if desired, modified in a suitable manner known to those skilled in the art. In particular, they do not constitute any restriction as to the protein which is to be purified. In view of the common structural features and general properties of the annexines, the process according to the invention is also applicable to the purification of the other annexines and it is especially suitable for purifying the annexines IBC, PAP, PAP I, PP4, endonexin, lipocortin V and VAC or an analog of VAC. Moreover, although the invention will be described with reference to obtaining VAC from a recombinant host, it may be used to obtain annexines from, for example, strongly vascularized tissue as taught in European Patent Application Publication No. 181 465, which is incorporated by reference in its entirety.

The following information regarding the reagents used are given by way of example and does not constitute any limitation on the invention claimed herein.

EXAMPLES

Example 1

1. BREAK UP OF CELLS:

Addition of Ca$^{++}$ and Lecithin, Washing and Extraction 122 g of frozen, non-inactivated cell mass of the clone *E.coli* HB101/pRH291 from fermentation No. 524 were thawed, suspended with 500 ml of lysing buffer by stirring (about 1 hour, cooling with ice) and then homogenized using the Ultra-Turrax T 45/6 (about 1 min, cooling with ice).

| LYSING BUFFER: | | |
|---|---|---|
| 100 mM TRIS | 12.14 g/1000 ml | Merck 8382 |
| 1 mM EDTA | 0.37 g/1000 ml | Titriplex III, Merck 8418 |
| 200 mM NaCl | 11.69 g/1000 ml | Merck 6404 |

The pH is adjusted to 9.0±0.1 using 32% HCl.
The suspension is homogenized three times at about 6000 psi using a Manton-Gaulin Press, Type 15M 8TA, in which the receiving vessel is cooled with ice. The apparatus is then washed twice with 150 to 200 ml of lysing buffer (total volume of extract: 1000 ml).

2. Addition of Ca$^{++}$ and lecithin for adsorption of VAC on the insoluble cell residue 0.55 g of calcium chloride (Merck 2083) freshly dissolved (final concentration 5 mM) and 6.1 ml of lecithin solution (200 mg/ml chloroform) are added to the homogenized material. Final concentration 1 g lecithin/100 g biomass.

The mixture is homogenized for one minute with the Ultra-Turrax and stirred for 60 minutes in an ice bath.
LECITHIN: lecithin from soya beans, pract., serva 57556

110 ml of 5% polyamine solution (prepared from 50% polyamine P, serva 33141, diluted to 5% and neutralized to pH 8 with 5N HCl) are then added and the mixture is stirred for a further 30 minutes. Final concentration 0.5%. The suspension is then centrifuged until clear (Beckman High Speed Centrifuge J2-21, Rotor JA 10, 8000 rpm, 30 min, setting 2° C).

SUPERNATANT I: 1020 ml (4.25 mg protein/ml; 0.05 mg VAC/ml).

3. Washing the cell residue to remove any soluble matter

The cell residue is suspended with 600 ml of washing buffer using the Ultra-Turrax and then stirred for 30 minutes.

| WASHING BUFFER: |
|---|
| 100 Mm Tris |
| 200 mM NaCl |
| 5 mM CaCl$_2$ |

The pH is adjusted to 9.0±0.1 used in 32% HCl. The cell residue is obtained by centrifuging as before.

SUPERNATANT II: 580 ml (1.35 mg protein/ml; 0.04 mg VAC/ml)

The suspension in 350 ml of washing buffer, subsequent homogenization and stirring are repeated once more. The mixture is then centrifuged.

SUPERNATANT III: 340 ml (0.93 mg protein/ml; 0.02 mg VAC/ml)

4. Extraction of VAC with buffer containing EDTA

The pellets are homogenized with 900 ml of extraction buffer in the Ultra-Turrax and then stirred overnight in a cold store. The extract is centrifuged as described and the clear solution, i.e. the crude extract, is obtained.

CRUDE EXTRACT: 915 ml (1.98 mg protein/ml; 0.65 mg VAC/ml)

EXTRACTION BUFFER

20 Mm TRIS
50 mM EDTA
The pH is adjusted with 5N NaOH to 7.5±0.1.

| SUMMARY OF THE WASHING PROCEDURE AND EXTRACTION | | | |
|---|---|---|---|
| SUPERNATANT I: | 1020 ml | 4335 mg protein | 49 mg VAC |
| SUPERNATANT II: | 580 ml | 783 mg protein | 22 mg VAC |
| SUPERNATANT III: | 340 ml | 316 mg protein | 5 mg VAC |
| | | 5434 mg protein | 76 mg VAC (11%) |
| CRUDE EXTRACT VAC | 915 ml | 1816 mg protein | 594 mg VAC |

| SUMMARY OF THE WASHING PROCEDURE AND EXTRACTION |
| --- |
| in 122 g of cell mass VAC total 670 mg (89%) |

Example 2

SUMMARY

1. Inactivation
2. Cell breakdown
3. Addition of Ca++ and lecithin for adsorption of VAC on the insoluble cell residue.
4. Washing of cell residue to eliminate soluble components.
5. Extraction of VAC with buffer containing EDTA.
6. Addition of 35% sat. ammonium sulphate and removal of the precipitate.
7. Chromatography on Phenyl-Sepharose Fast Flow.
8. Dialysis of the VAC-Pools and chromatography on Q-Sepharose Fast Flow.
9. Concentration of the VAC-Pool and chromatography on sephacryl S-200 HR.

1. Inactivation

The end of fermentation is achieved after about 17 hours from the consumption of the phosphate in the medium. At this time, 10 mM $CaCl_2$ are added and the temperature is adjusted to the fastest possible cooling to 5° to 8° C. All the other regulated parameters (such as aeration stirring, pH, pressure, etc) stay the same. After about 10 minutes, 7 ml/1 of m-cresol are added, then the pressure, aeration and pH adjustment are switched off and the stirring is reduced to a level which will ensure that the fermentation liquor is properly mixed with the cresol but the formation of foam is limited. Under these conditions, inactivation is carried out for at least 3 and not more than 15 hours (temperature remaining at 5° to 8° C).

2. Cell Breakdown

Addition of Ca++ and Lecithin, Washing and Extraction 286 g of frozen cell mass of the clone HB101/pGN25, inactivated with m-cresol, are thawed and suspended with 750 ml of lysing buffer by stirring (about 1 hour, cooling with ice) and then homogenized using the Ultra-Turrax T 45/6 (about 1 min, cooling with ice).

| LYSING BUFFER: |
| --- |
| 100 mM TRIS |
| 1 mM EDTA |
| 200 mM NaCl |

The pH is adjusted to 9.0±0.1 with 32% HCl. The suspension is homogenized three times at about 6000 psi using a Manton-Gaulin Press, Type 15M 8TA, with the receiving vessel cooled in ice. The apparatus is then washed twice with 150 to 200 ml of lysing buffer. Volume of homogenized material: 1400 ml.

2. Addition of Ca++ and Lecithin for the adsorption of VAC on the insoluble cell residue 0.55 g of $CaCl_2$ (Merck 2083)/1000 ml (final concentration 5 mM) are added to the homogenized material (dissolved in about 10 ml of $H_2O$) and 1 g of lecithin/100 g of biomass, dissolved in chloroform (about 0.2 g/ml) are added.

The mixture is homogenized for one minute using the Ultra-Turrax and stirred for 60 minutes in an ice bath.

LECITHIN: lecithin from soya beans, pract., serva 57556

0.11 Volumes of 5% polyamine solution (prepared from 50% polyamine P, serva 33141, diluted to 5% and neutralized to pH 8 with 5N HCl) are then added and the mixture is stirred for a further 30 minutes. Final concentration 0.5%. The suspension is then centrifuged until clear (Beckman High Speed Centrifuge J2-21, Rotor JA 10, 8000 rpm, 30 min, setting 2° C.)

SUPERNATANT I: 1200 ml (5.8 mg protein/ml; 0.01 mg VAC/ml).

3. Washing of cell residue to eliminate soluble matter

The cell residue is suspended with about 1000 ml of washing buffer using the Ultra-Turrax and then stirred for 30 minutes.

| WASHING BUFFER: |
| --- |
| 100 Mm Tris |
| 200 mM NaCl |
| 5 mM $CaCl_2$ |

The pH is adjusted to 9.0±0.1 using 32% HCl.
The cell residue is obtained by centrifuging as before.
SUPERNATANT II: 1000 ml (1.94 mg protein/ml; 0.01 mg VAC/ml)

The suspension in 1000 ml of washing buffer, followed by homogenizing and stirring is repeated once more and finally centrifugation is carried out.

SUPERNATANT III: 1000 ml (0.79 mg protein/ml; 0.01 mg VAC/ml)

4. Extraction of VAC with EDTA containing buffer

The pellets are homogenized with 1350 ml of extraction buffer in the Ultra-Turrax and then stirred overnight in a cold store. The extract is centrifuged as described and the clear solution, i.e. the crude extract is obtained.

CRUDE EXTRACT: 1350 ml (3.35 mg protein/ml; 1.46 mg VAC/ml)

| EXTRACTION BUFFER: |
| --- |
| 20 Mm TRIS |
| 50 mM EDTA |

The pH is adjusted to 7.5±0.1 using 5N NaOH.

| SUMMARY OF THE WASHING PROCEDURE AND EXTRACTION | | | |
| --- | --- | --- | --- |
| SUPERNATANT I: | 1,200 ml | 6,960 mg protein | 12 mg VAC |
| SUPERNATANT II: | 1,000 ml | 1,940 mg protein | 10 mg VAC |
| SUPERNATANT III: | 1,000 ml | 790 mg protein | 10 mg VAC |
| | | 9,690 mg protein | 32 mg VAC (2%) |
| CRUDE EXTRACT VAC | 1,350 ml | 4,522 mg protein | 1,971 mg VAC |
| in 286 g of cell mass VAC total 2003 mg (98%) | | | |

5-6. Precipitation at 35° With Sat. Ammonium Sulphate and Chromatography on Phenyl-Sepharose Fast Flow Precipitation with Ammonium Sulphate 209 g/l of solid ammonium sulphate (Merck 1217) are slowly added to the crude extract with stirring. This produces a saturation level of 35%. After at least 1 hour's stirring in the cold store the solution is centrifuged until clear (under the same conditions as before) and the precipitate is discarded. The solution is pumped at a speed of 8-10 ml/min using the FPLC apparatus onto the prepared phenyl sepharose FF.

The centrifuged 35% sat. ammonium sulphate supernatant is further processed in two approximately equal batches and all subsequent purification steps are carried out twice in succession.

Preparation of the column

A Pharmacia Column, Type XK 26/40 (bed volume about 200 ml) is filled with Phenyl-Sepharose Fast Flow (Pharmacia, Code No. 17-0965) and equilibrated with buffer A. Two to three CV (Column Volumes) of buffer are required for this. The column is connected to a FPLC apparatus. All the chromatography is carried out at ambient temperature.

| BUFFER A: |
|---|
| 50 Mm TRIS |

The buffer is adjusted to pH 7.2±0.1 using conc HCl. Then 209 g/1000 ml of solid ammonium sulphate (Merck 1217) are added.

BUFFER B

Like buffer A, but with no ammonium sulphate added.

Chromatography

The eluate is monitored by measuring the O.D. 280 nm. As soon as the preparation has been applied to the column, it is washed with buffer A until the O.D. 280 nm returns to its original value. Then a gradient buffer A buffer B of 0 to 100% B of 5 column volumes (1000 ml) is used to elute the bound VAC. VAC is the first prominent peak after the start of the gradient (see the picture of the elution diagram; FIG. 1). Aliquots of the through flow, the VAC-Pool and any other peaks of the O.D. profile are investigated by SDS-PAGE. Testing of the VAC-Pool: protein determination, VAC-testing, SDS-PAGE.

Regeneration of the Column

The phenyl sepharose is regenerated with two volumes of 6M urea. After the urea has been washed out (1 CV of distilled water) it is stored in 24% ethanol.

In order to remove or avoid any colored components at the top end of the column, a more extensive washing and regeneration process is used:
1. 1 CV distilled water
2. 2 CV 6M urea (Merck 8487)
3. 1 CV distilled water
4. 1 CV 0.1M NaOH
6. Equilibrated before use with 3 CV buffer A
7. Chromatography on Q-Sepharose Fast Flow In order to avoid using too much buffer in the dialysis of the VAC-Pool with the application buffer of the Q sepharose, the Pool is first concentrated in an AMICON-Ultrafiltration cell and a YM 10-filter: down to about 150 ml. It is then dialyzed with buffer A.

| BUFFER A: |
|---|
| 20 mM Bis-TRIS |
| The pH is adjusted to 6.3 ± 0.1 using 5 N HCl. |
| BUFFER B: |
| Buffer A + 0.35 M NaCl |
| 20 mM Bis-TRIS |
| 350 mM NaCl |

The pH is adjusted to 6.3±0.1 using 5N HCl.

Preparation of Column

A type HR 16/50 Pharmacia Column (CV 100 ml) is connected up to the FPLC system and filled with Q-Sepharose Fast Flow (Pharmacia) using the filling device. It is equilibrated with 2 CV buffer A. Chromatography is carried out at an ambient temperature.

Chromatography

The sample is applied at the rate of 4 ml/min. It is then washed with buffer A until the O.D. 280 nm of the eluate falls to the original value. The gradient program is as follows:
0.5 CV 0-30% B
8.0 CV 30-70% B (separation is carried out here)
about 1.0 CV 100% B

Washing Program

When no UV-activated material is eluted at 100% B, the washing program begins:
2 CV distilled water
2 CV 0.5 n NaOH
2 CV distilled water
Storage: 24% ethanol
before use it is washed with 2-3 CV of buffer A:
control pH=6.3

Figure 2:
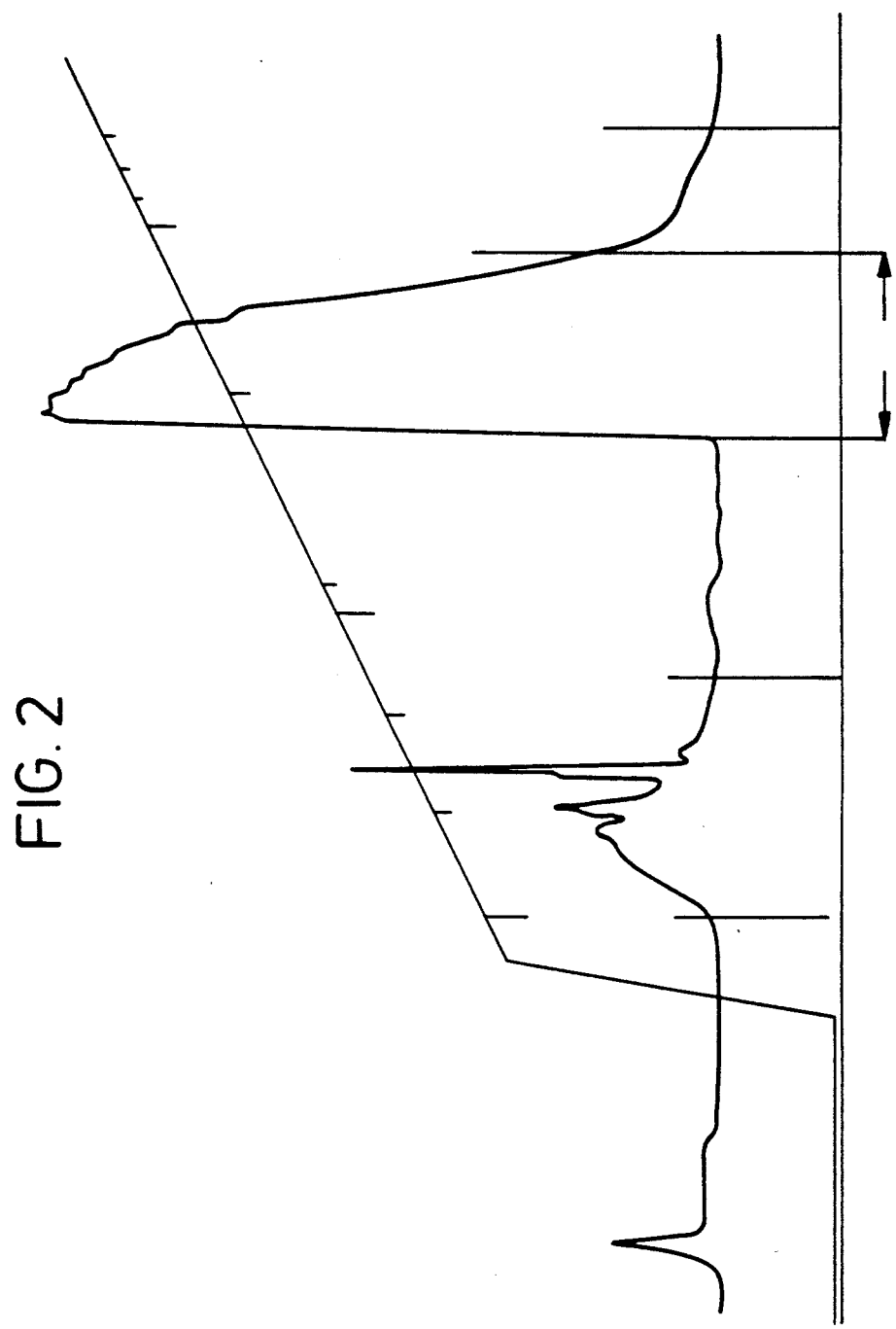
FIG. 2 depicts a chromatography elution profile on Q-Sepharose Fast Flow (←→=VAC-Pool).

The impurities are eluted in the program before the VAC. The elution profile is attached hereto (FIG. 2).
8. Chromatography on SEPHACRYL S-200 HR The VAC-Pool is concentrated to about 10 ml using an AMICON-Ultrafilter YM 10. It is found that VAC can be concentrated down to 100 mg/ml (BioRad) without any problem.

Column Preparation

A K 26/100 column made by Pharmacia with a bed volume of about 400 ml is filled with sephacryl S-200 high resolution (Pharmacia) in accordance with the instructions and equilibrated with an elution buffer (2 CV).

| ELUTION BUFFER: |
|---|
| 20 mM Na-phosphate pH = 7.2 |
| 150 mM NaCl |
| 20 mM sodium salt of succinic acid (pH = 7.0) |
| 0.01% Tween 20 |

Chromatography

Chromatography is carried out in the cold store. The flow rate is 80 ml/hour. The peak recorded at O.D. 280 nm is collected. The VAC purified in this way was more than 99% pure (RP-HPLC analysis).

Regeneration of the Sephacryl Column:

Washing program:

-continued

1 CV distilled water
2 CV 0.5 N NaOH (+ storage for some days)
(For lengthier storage it is advisable to use 1M
NaCl + 0.0025% NaOH)
Regeneration:
1 CV distilled water
2 CV elution buffer Summary of the Entire Purification

| Purification Step | Volume (ml) | Protein[x] (mg) | VAC-alpha[xx] (mg) |
|---|---|---|---|
| Supernatant I | 1,200 | 6,960 | 12 |
| Supernatant II | 1,000 | 1,940 | 10 |
| Supernatant III | 1,000 | 790 | 10 |
| Crude Extract | 1,350 | 4,522 | 1,971 |
| Supernatant 35% sat. Am$_2$SO$_4$ | 1,500 | 4,500 | 2,098 |
| Phenyl seph. FF-Pool | 975 | 3,050 | 2,041 |
| Load Q seph. FF | 355 | 3,062 | 2,277 |
| Q seph. FF-Pool | 475 | 2,660 | 2,082 |
| Load seph. S-200 HR | 23.7 | 2,446 (1,859)[xxx] | n.d. |
| Seph. S-200 HR-Pool | 192 | 2,477 (1,883) | 2,126 |

[x]Biorad protein assay (standard: bovine serum albumin)
[xx]VAC alpha assay: inhibition of formation of thrombin from prothrombin (Reutelingsperger, Hornstra and Hemker, Eur. J. Biochem. 151: 625-629 (1985)). A purified VAC alpha preparation was used as control.
[xxx]Protein content determined by measuring the O.D. 280 nm using the factor determined for pure VAC alpha: O.D. 280 nm × 1.277 = mg/ml VAC-alpha.

Example 3 Purification of the crude EDTA Extract with BPA

The purification described in Examples 1 and 2 was carried out, up to the extraction with buffer containing EDTA (step 4). The starting material was 295 g and 240 g of biomass, respectively.

After the crude extract had been obtained, 10% by volume of BPA 1000 were added and the mixture was stirred for 10 minutes. The precipitate formed was removed by centrifuging (High-Speed centrifuge made by Beckman, Rotor JA 10, 8000 rpm, 30 min. at 2° C.).

Further purification was carried out as follows:

Addition of solid ammonium sulfate to 35% saturation and further chromatography on phenyl sepharose Fast Flow (see instructions given hereinbefore).

Results for VAC alpha

| Step: | Vol. (ml) | Protein (mg/ml) | VACalpha (mg/ml-total) | ECP (ppm) |
|---|---|---|---|---|
| Starting material: 295 g of biomass (batch B005001) | | | | |
| Crude Extract | 700 | 4.0 | 1.87 (1309) | 126,000 |
| After BPA 100 | 700 | 2.7 | 1.77 (1239) | 11,700 |
| Phenyl Sepharose Fast Flow Pool | 215 | 3.23 | 4.23 (909) | n.d. |
| Q-Sepharose Fast Flow Pool | 169 | 3.83 | 4.70 (794) | 39 |
| Sephacryl S-200 HR Pool (endproduct) | 59.7 | 10.4 | 10.9 (651) | 41 |
| Starting material: 240 g of biomass (batch B005001) | | | | |
| Crude Extract | 680 | 3.20 | 1.58 (1309) | 776,000 |
| After BPA 100 | 680 | 2.00 | 0.95 (646) | 19,600 |
| Phenyl Sepharose Fast Flow Pool | 205 | 3.73 | 2.86 (586) | 2,370 |
| Q-Sepharose Fast Flow Pool | 150 | 4.55 | 3.40 (510) | 45 |
| Sephacryl S-200 HR Pool (endproduct) | 56.0 | 7.10 | 7.40 (414) | 35 |

What is claimed is:

1. A process for purifying an annexine, consisting essentially of the steps of:
   (a) obtaining cells which express an annexine,
   (b) preparing a homogenized cell preparation of said cells and adjusting the pH to about 8.0 to about 10.0,
   (c) adding at least one bivalent cation selected from the group consisting of $Ca^{2+}$, $Cd^{2+}$, $Zn^{2+}$, $Mn^{2+}$ and $Co^{2+}$,
   (d) adding a phospholipid,
   (e) washing the insoluble cell residue to remove the soluble constituents, and
   (f) extracting the annexine from the cell residue with a chelating agent.

2. The process according to claim 1, further comprising:
   (g) adding a resin having ionizable groups to the extracted annexine obtained in step (f), and
   (h) separating the resulting precipitate.

3. The process according to claim 2, wherein said resin is functionalized with cationic groups.

4. The process according to claim 1, wherein the annexine obtained in step f) is further purified by protein precipitation and subsequent chromotographic separation.

5. The process according to claim 1, wherein the pH is adjusted to about 9.0 in step b).

6. The process according to claim 1, wherein said at least one bivalent cation added in step c) is $Ca^{2+}$.

7. The process according to claim 1, wherein said at least one divalent cation added in step c) is $Ca^{2+}$ and $Zn^{2+}$.

8. The process according to claim 1, wherein said phospholipid added in step d) is lecithin.

9. The process according to claim 1, wherein step c) and step d) are carried out substantially simultaneously.

10. The process according to claim 1, wherein said chelating agent in step f) is EDTA.

11. The process according to claim 1, wherein said homogenized preparation of step b) is obtained by first inactivating cells which express the annexine and then homogenizing the inactivated cells.

12. The process according to claim 11, wherein said cells are inactivated by treatment with an aromatic compound selected from the group consisting of benzene, toluene, phenol, xylene and cresol.

13. The process according to claim 12, wherein said cells are inactivated with m-cresol.

14. The process according to claim 1, wherein said annexine is a VAC.

15. A process for purifying a VAC, consisting essentially of the steps of:
   (a) obtaining cells which express a VAC,
   (b) inactivating and homogenizing said cells and adjusting the pH to about 9.0.
   (c) adding $Ca^{2+}$,
   (d) adding lecithin,
   (e) washing the insoluble cell residue to remove the soluble constituents, and
   (f) extracting the VAC from the cell residue with EDTA.

16. The process according to claim 15, further comprising:
   (g) adding a resin having ionizable groups to the extracted annexine obtained in step (f), and
   (h) separating the resulting precipitate.

17. The process according to claim 16, wherein said resin is functionalized with cationic groups.

18. The process according to claim 15, wherein step c) and step d) are carried out substantially simultaneously.

19. The process according to claim 15, wherein said inactivating is accomplished by the addition of m-cresol.

20. The process according to claim 1, wherein said at least one divalent cation added in step c) is $Zn^{2+}$.

* * * * *

UNITED STATES PATENT AND TRADEMARK OFFICE
CERTIFICATE OF CORRECTION

PATENT NO. : 5,258,497

DATED : November 2, 1993

INVENTOR(S) : REUTELINGSPERGER et al.

It is certified that error appears in the above-identified patent and that said Letters Patent is hereby corrected as shown below:

Column 9, before line 62, insert --5. Washing and storage in 24% ethanol--.

Signed and Sealed this

Twenty-eighth Day of June, 1994

Attest:

BRUCE LEHMAN

Attesting Officer

Commissioner of Patents and Trademarks